US009498455B2

(12) United States Patent
De Torres Gómez-Pallete

(10) Patent No.: US 9,498,455 B2
(45) Date of Patent: Nov. 22, 2016

(54) CINACALCET AND NEUROBLASTIC TUMOURS

(71) Applicants: HOSPITAL SAINT JOAN DE DEU, Esplugues de Llobregat (ES); FUNDACIÓ CELLEX, Barcelona (ES)

(72) Inventor: Carmen De Torres Gómez-Pallete, Esplugues de Llobregat (ES)

(73) Assignees: HOSPITAL SANT JOAN DE DEU, Barcelona (ES); FUNDACIÓ CELLEX, Barcelona (ES)

( * ) Notice: Subject to any disclaimer, the term of this patent is extended or adjusted under 35 U.S.C. 154(b) by 0 days.

(21) Appl. No.: 14/420,731

(22) PCT Filed: Jan. 21, 2013

(86) PCT No.: PCT/ES2013/070019
§ 371 (c)(1),
(2) Date: Feb. 10, 2015

(87) PCT Pub. No.: WO2013/144397
PCT Pub. Date: Oct. 3, 2013

(65) Prior Publication Data
US 2015/0342907 A1 Dec. 3, 2015

(30) Foreign Application Priority Data
Mar. 29, 2012 (ES) .................................. 201230476

(51) Int. Cl.
*A61K 31/137* (2006.01)
(52) U.S. Cl.
CPC .................................. *A61K 31/137* (2013.01)
(58) Field of Classification Search
USPC ................................. 514/579, 646, 649, 741
See application file for complete search history.

(56) References Cited

U.S. PATENT DOCUMENTS

| | | | |
|---|---|---|---|
| 5,688,938 A | 11/1997 | Brown | |
| 6,296,833 B1 | 10/2001 | Brown | |
| 2002/0132224 A1 | 9/2002 | Poznansky | |
| 2011/0097338 A1* | 4/2011 | Cordes | A61K 39/39558 424/156.1 |

FOREIGN PATENT DOCUMENTS

| | | |
|---|---|---|
| EP | 2286836 A1 | 2/2011 |
| WO | 9938500 A2 | 8/1999 |
| WO | 2008075173 A2 | 6/2008 |
| WO | 2010063847 A1 | 6/2010 |

OTHER PUBLICATIONS

European Search for corresponding application EP 13 76 9054; Report dated Sep. 29, 2015.
Grace Poon, "Cinacalet hydrochloride (Sensipar)" Proceedings, Baylor University Medical Center, Apr. 2005, vol. 18, No. 2, pp. 181-184, XP002744488.
International Search Report for corresponding application PCT/ES2013/070019 filed Jan. 21, 2013; Mail date Jul. 2, 2013.
Torres, et al., "The calcium-sensing receptor and parathyroid-related protein are expressed in differentiated, favorable neuroblastic tumors", Cancer (2009)vol. 115, p. 2792-2803.
International Preliminary Report on Patentability for International Application PCT/ES/2013/070019; International Filing Date: Jan. 21, 2013; Date report issued: Oct. 1, 2014; 6 pages.
International Search Report for International Application PCT/ES2013/070019; International Filing Date; Jan. 21, 2013; Mailing Date of Report: Jul. 2, 2013; 6 pages.
Written Opinion of the International Searching Authority for International Application PCT/ES2013/070019; International Filing Date; Jan. 21, 2013; Date of mailing Jul. 2, 2013; 5 pages.

* cited by examiner

*Primary Examiner* — Pancham Bakshi
(74) *Attorney, Agent, or Firm* — Cantor Colburn LLP

(57) ABSTRACT

The present invention relates to the field of pediatric or childhood tumor therapy. More specifically, the invention relates to the use of the allosteric activator of the calcium sensor receptor, cinacalcet, for the preparation of a pharmaceutical product for the treatment of neuroblastic tumors, particularly for the treatment of neuroblastomas, ganglioneuroblastomas and ganglioneuromas.

4 Claims, 6 Drawing Sheets

CINACALCET AND NEUROBLASTIC TUMOURS

FIELD OF THE INVENTION

The present invention relates to the field of pediatric or childhood tumors. Specifically, the invention relates to the use of the allosteric activator of the calcium sensor receptor, cinacalcet, for the preparation of a pharmaceutical product for the treatment of neuroblastic tumors.

BACKGROUND OF THE INVENTION

Tumors manifesting mainly at the pediatric age or manifesting only at this stage are known as childhood tumors. For this reason, they are also sometimes referred to as pediatric tumors. In the context of the present invention, the term childhood tumor or pediatric tumor will be used interchangeably.

The group of childhood tumors includes neuroblastomas (NBs), ganglioneuroblastomas (GNBs) and ganglioneuromas (GNs), forming the group of neuroblastic tumors (NTs). Neuroblastic tumors are the most common solid extracranial childhood tumors that develop from neural crest cells which have already been compromised during peripheral nervous system formation, so they are localized in the adrenal medulla or in the ganglia of the paravertebral sympathetic chain. Most localized NBs, GNBs and GNs have excellent survival rates, but today metastatic NBs have survival rates of about 40% despite being subjected to intensive multi-modal therapies.

Neuroblastic tumors are a group of highly heterogeneous tumors from the clinical, anatomopathological, genetic and biological viewpoint. The biological bases responsible for the clinical diversity of NTs are only partially known, but they are without a doubt behind the different ways in which tumors respond to treatment protocols. Among them, ploidy alterations, unbalanced translocations, recurrent chromosome region deletions or additions and MYCN oncogene amplification, stand out. These genetic-molecular alterations can hardly be modified therapeutically although they are crucial for the biological behavior of NTs. Before describing them further, it was already known that highly differentiated NTs with a higher proportion of Schwann-type stromal component (NB in differentiation, GNB and GN) were associated with a better prognosis than undifferentiated NBs. Some of the molecular pathways responsible for cell differentiation processes in NT have been discovered. These pathways are of great therapeutic importance since they can be pharmacologically modulated. Therefore, for example, retinoic acid induces differentiation in NB cell lines and in patient tumors, improving overall survival of a patient sub-group. Some NBs are resistant to the action of this drug, but the lack of in-depth knowledge about the molecular mechanisms responsible for NT differentiation complicates the design of new differentiating agents that can benefit a large number of patients.

The calcium sensor receptor gene (CASR) was cloned in 1993 from bovine parathyroid cells and is part of the C family of the G protein-coupled receptor (GPCR) superfamily, along with eight glutamate receptors, two GABA-B receptors, some taste receptors and GPRC6A amino acid sensor. This family of receptors detects signals from ions, amino acids and nutrients, among others, and transmits them to the intracellular medium. They all share a similar structure consisting of a large extracellular amino-terminal domain, seven transmembrane helices and an intracellular carboxyl-terminal tail. In the case of CASR, its main function is to detect the fluctuations of extracellular $Ca^{2+}$ and accordingly regulate the secretion of parathyroid hormone (PTH) in parathyroid glands and calcitonin in thyroid C cells, which hormones are responsible for normalizing calcemia. In the context of the parathyroid, CASR activation by calcium translates into a drop in parathyroid hormone (PTH) regulation and production, which will in turn reduce plasma calcium concentration to keep it within a narrow margin (1.1-1.3 mM).

CASR expression has been found in different neoplasias with the particularity that they attribute very different, even opposing functions, thereto in different tumor contexts. Therefore, for example, it has been described that CASR activation promotes prostate carcinoma proliferation and metastasis, whereas data seems to support that it participates in colon carcinoma differentiation processes.

There are direct CASR agonists (or type 1 agonists) and allosteric activators of CASR (or type 2 agonists). Direct CASR agonists such as $Ca^{2+}$, $Mg^{2+}$, $Gd^{3+}$, neomycin, L-amino acids, activate CASR by means of direct interaction with the extracellular domain thereof. In contrast, allosteric activators do not activate the receptor per se but rather change its three-dimensional structure, such that it becomes more sensitive to the calcium stimulus. Cinacalcet is an allosteric activator of the calcium sensor receptor. U.S. Pat. No. 5,688,938 describes several CASR agonists, such as NPS R-467 and NPS R-568, NPS R-568 (also referred to as R-568) being the most active. Likewise, U.S. Pat. No. 6,296,833 describes the use of calcium agonists or antagonists for the treatment of cancer. The present application describes the use of cinacalcet for the preparation of a pharmaceutical product for the treatment of neuroblastic tumors. Surprisingly, the use of cinacalcet results in significant advantages because it is capable of inducing tumor cell apoptosis at a lower concentration than other CASR agonists.

Object of the Invention

The present invention relates to the use of cinacalcet for the preparation of a pharmaceutical product for the treatment of neuroblastic tumors, particularly for the treatment of neuroblastomas, ganglioneuroblastomas and ganglioneuromas.

DETAILED DESCRIPTION OF THE INVENTION

In one aspect, the present invention relates to the use of cinacalcet for the preparation of a pharmaceutical product for the treatment of neuroblastic tumors. In a particular embodiment, the present invention relates to the use of cinacalcet for the preparation of a pharmaceutical product for the treatment of neuroblastomas. In another particular embodiment, the present invention relates to the use of cinacalcet for the preparation of a pharmaceutical product for the treatment of ganglioneuroblastomas. In another particular embodiment, the present invention relates to the use of cinacalcet for the preparation of a pharmaceutical product for the treatment of ganglioneuromas.

In another aspect, the present invention relates to cinacalcet for use in the treatment of neuroblastic tumors, particularly for use in the treatment of neuroblastomas. In another particular embodiment, the present invention relates to cinacalcet for use in the treatment of ganglioneuroblastomas, and in another particular embodiment, the present invention relates to cinacalcet for use in the treatment of ganglioneuromas.

As mentioned in the background section, U.S. Pat. No. 5,688,938 describes NPS R-568 as the most active CASR agonist compound. In that regard, comparative assays have been carried out in the present invention to compare the effects of using cinacalcet and R-568 in the treatment of neuroblastic tumors. Surprisingly, cinacalcet has a series of advantages with respect to NPS R-568 from the pharmacological and pharmacodynamic viewpoint. One of the most significant and surprising effects of cinacalcet is apoptosis induction at concentrations that are significantly lower than NPS R-568 (FIG. 2, Table 1). This entails significant advantages of cinacalcet with respect to other CASR agonists since it allows effective treatment with the administration of a lower dose of pharmaceutical product, which generally involves greater treatment tolerance and less risk of occurrence of side effects or toxicity, in addition to facilitating administration and administration regimen. These advantages are particularly relevant when a drug must be administered in a prolonged manner over time, as is the case of cinacalcet administered for the treatment of neuroblastic tumors. Relapses of These tumors occur frequently, so it is predictable that this treatment, like other treatments used in the context of minimal residual disease to prevent relapse, must be administered continuously for a long time period. Likewise, it is possible that if a tumor has responded suitably to initial treatment with cinacalcet, it can benefit from re-use of this drug in the event of recurrence (after initial remission), a strategy that has been shown to be useful with various treatments in oncology (rechallenging).

EXAMPLES

Specific embodiments of the invention that serve to illustrate the invention are described in detail below.

Example 1

Figure 1:
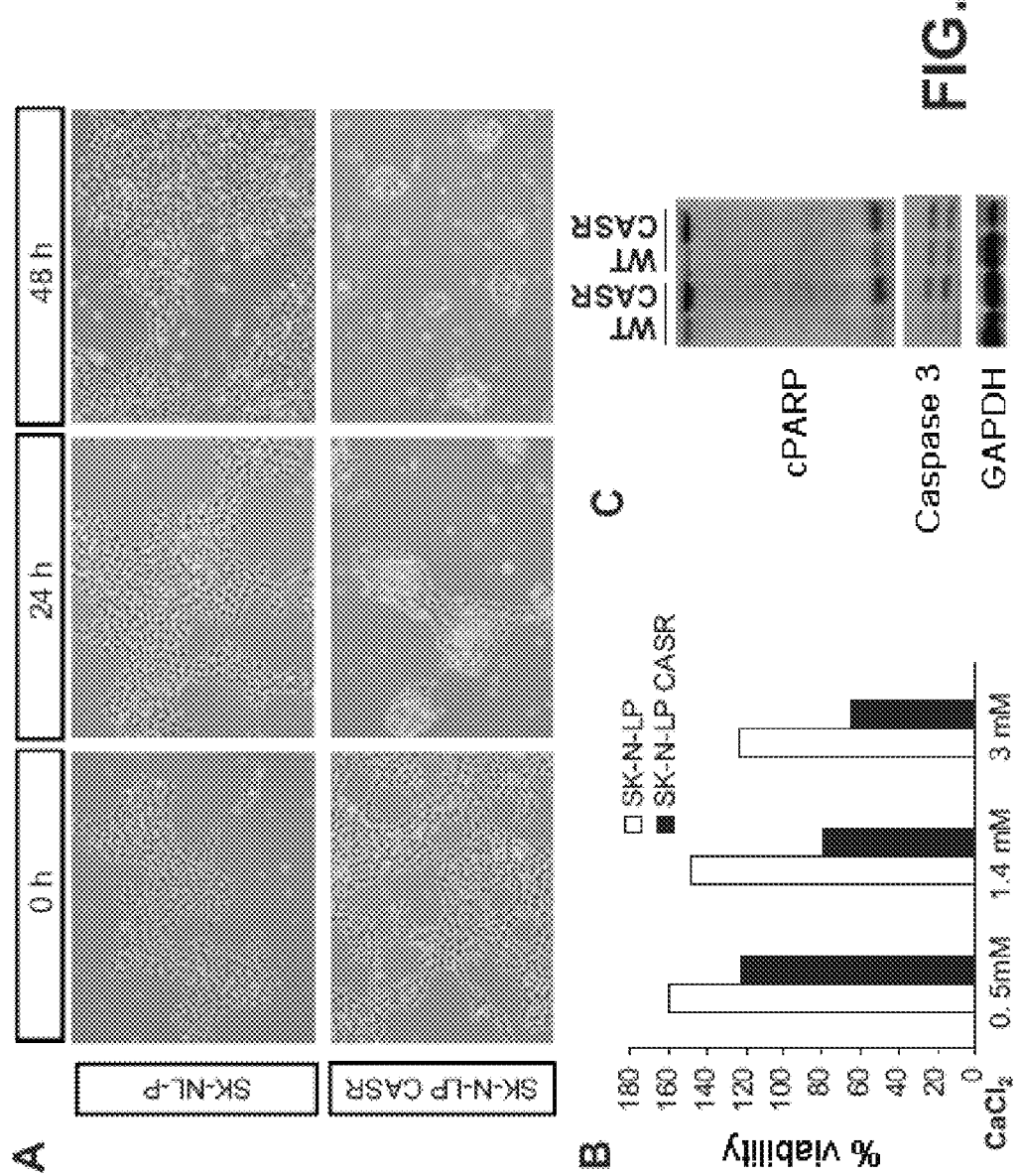
FIG. 1A shows the morphology of SK-N-LP cells with (bottom panels) or without (top panels) overexpression of CASR after being subjected for 16 hours to serum deprivation and subsequent exposure to 3 mM $CaCl_2$ for 24 and 48 hours.
FIG. 1B shows cell viability analysis in the SK-N-LP cell line with overexpression of CASR (black bar) or without overexpression of CASR (white bar) after 16 hours of serum deprivation and subsequent exposure to 0.5 mM, 1.4 mM or 3 mM $CaCl_2$ for 48 hours.
FIG. 1C shows Western blot analysis of caspase 3 activation and PARP cleavage in wild type SK-N-LP cells (WT) and in SK-N-LP cells with overexpression of CASR (CASR) after being exposed for 24 hours (first two lanes) and 48 hours (last two lanes) to the in vitro model described for FIG. 1A.
Figure 2A:
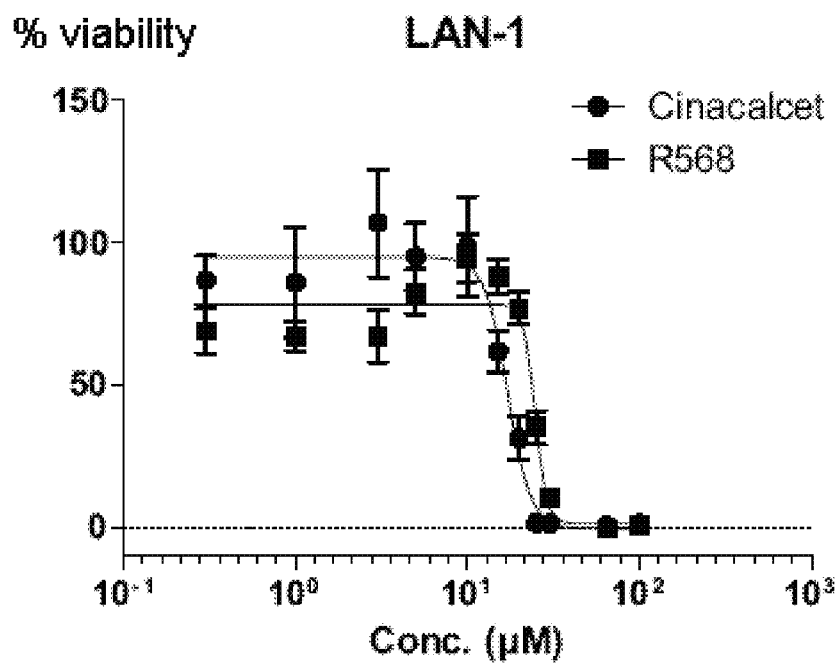
FIG. 2 shows cell viability of wild type neuroblastoma cell lines treated in vitro with cinacalcet or with NPS R-568 for 72 hours. The percentage of viability with respect to the control over the concentration (Conc.) in µM of cinacalcet (circle) or R-568 (square) is depicted. The analyzed cell lines are the following: LAN-1 (FIG. 2A), SK-N-LP (FIG. 2B), SK-N-JD (FIG. 2C), SK-N-BE(2)c (FIG. 2D), LA1-5s (FIG. 2E), LA1-55n (FIG. 2F) and SK-N-AS (FIG. 2G).
Figure 2B:
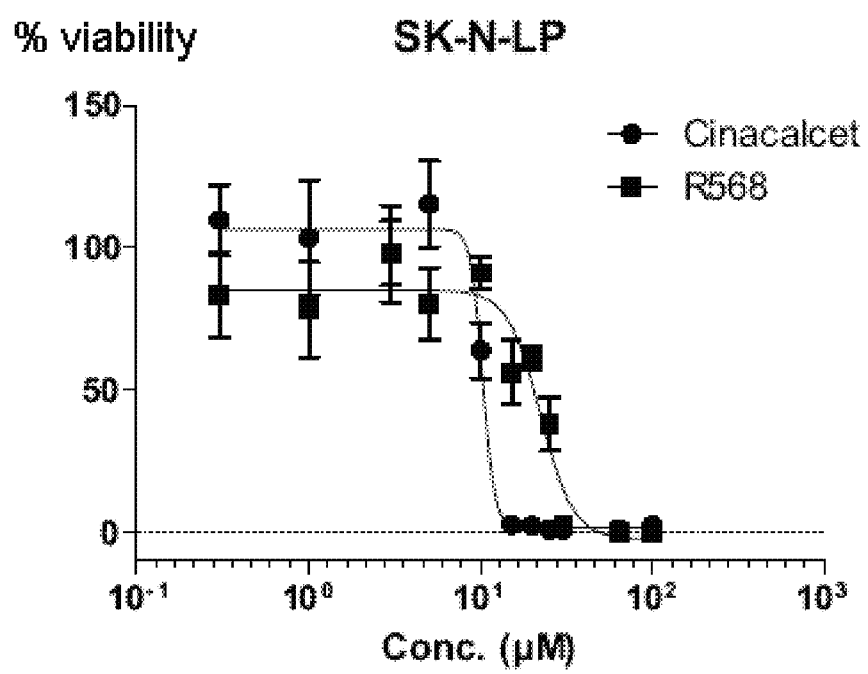
Figure 2C:
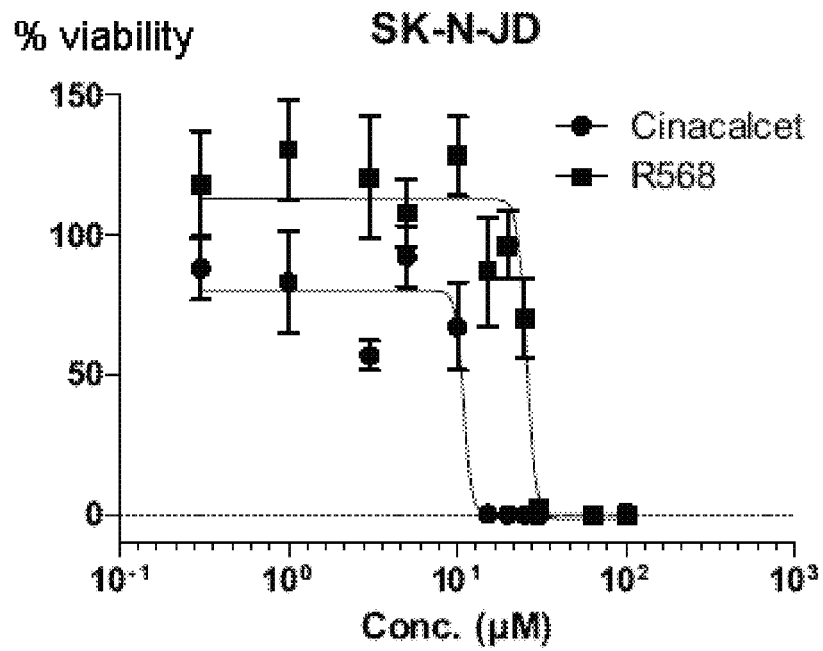
Figure 2D:
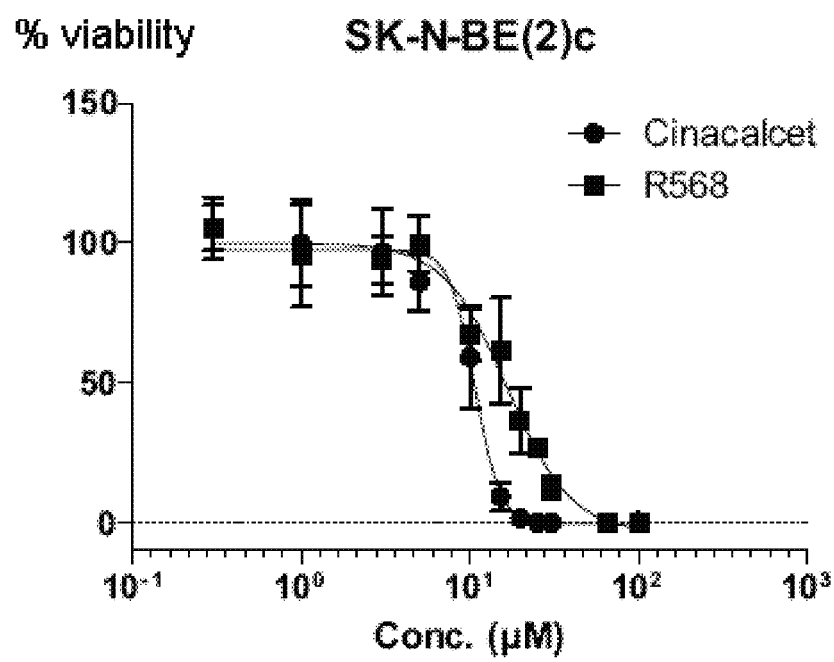
Figure 2E:
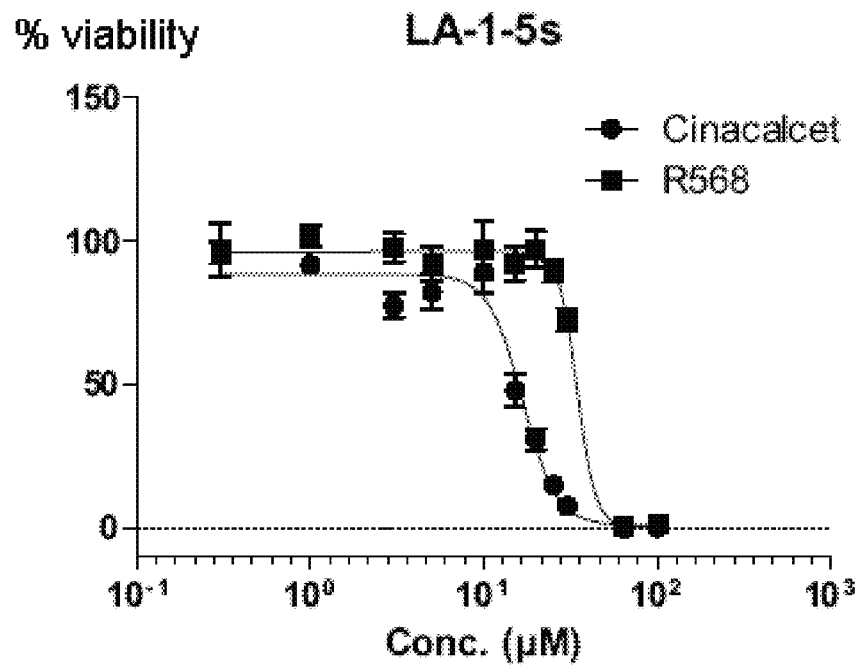
Figure 2F:
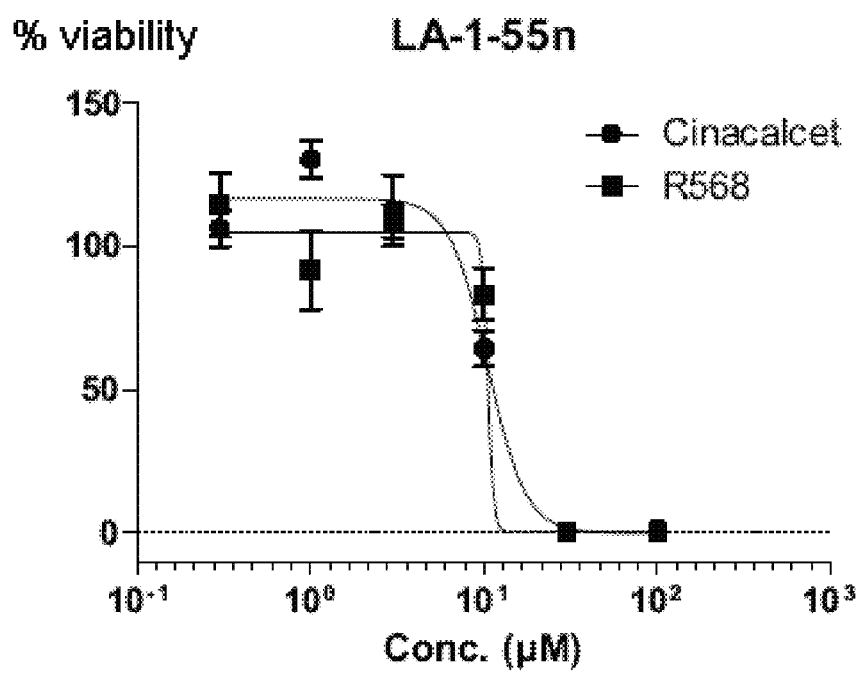
Figure 2G:
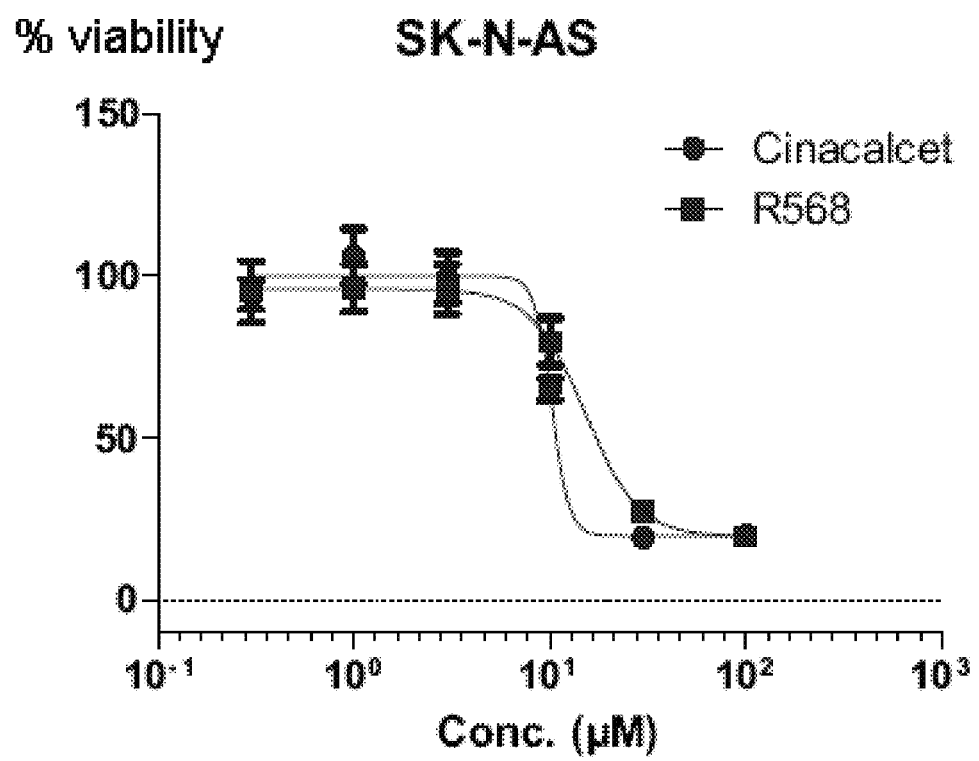

Analysis of the Effects Promoted In Vitro by CASR Activation by Means of Calcium in Neuroblastoma Cell Lines with or without Overexpression of CASR Wild type SK-N-LP cells stably transfected with pCMV-GFP or pCMV-CASR-GFP ($1\times10^6$) in RPMI 10% FBS were seeded in P100 plates. The medium was substituted the next day with a serum-free medium (calcium-free DMEM supplemented with 0.2% bovine albumin, 4 mM L-glutamine and 0.5 mM $CaCl_2$). This was maintained for 16 hours before substituting it with the same medium supplemented or not supplemented with up to 3 mM $CaCl_2$. It was thus observed that cells with overexpression of CASR suffered cell death in this model when they were exposed to 3 mM $CaCl_2$ (FIG. 1A, bottom panel) but not to 0.5 mM (data not shown). This phenomenon, which started about 6 hours after treatment with calcium and was very significant after 48 hours, was hardly appreciable in wild type cell lines or cell lines transfected with pCMV-GFP (FIG. 1A, top panel). In the latter cell lines, indications of cell death were detected, but the cells continued to proliferate until reaching confluence, whereas cells with overexpression of CASR completely disappeared in 5 days.

To quantify the decrease in cell viability, the same model was carried out in 24-well plates in the aforementioned lines and clones (FIG. 1B). After 48 hours, the percentage of viable cells was quantified by means of Promega CellTiter 96(r) Aqueous One Solution Cell Proliferation Assay (MTS) system. It was thus observed that the cell viability of cells with overexpression of CASR (black bar, FIG. 1B) decreased significantly more than that of the wild type SK-N-LP cell line (white bar, FIG. 1B).

In order to determine if the cell death process occurred by means of apoptosis, total proteins of wild type SK-N-LP cells (WT) and cells with overexpression of CASR (CASR) were extracted 24 and 48 hours after exposure to this model. The proteins were subjected to SDS-PAGE gel electrophoresis, transferred to a nitrocellulose membrane and incubated with specific antibodies to detect activated caspase 3 and c-PARP (Cell Signaling). Suitable secondary antibodies labeled with peroxidase were used, and it was developed with the Amersham ECL system. It was therefore clearly shown that cell death induced by activation of CASR by means of calcium is accompanied by caspase 3 activation and PARP cleavage (FIG. 1C), which is compatible with apoptotic cell death.

Example 2

Analysis of the Effects on Cell Viability Promoted In Vitro by Cinacalcet and NPS R-568 in Seven Neuroblastoma Cell Lines $5\times10^3$ cells of each cell line (LAN-1, SK-N-BE(2)c, LA1-55n, LA1-5s, SK-N-LP, SK-N-JD, SK-N-AS) were seeded in 96-well plates (6 replicates per condition). The initial medium (RPMI 10% FBS) was removed the next day and substituted with the same medium containing several concentrations (100 µM, 65 µM, 30 µM, 25 µM, 20 µM, 15 µM, 10 µM, 5 µM, 3 µM, 1 µM, 0.3 µM) of cinacalcet (Selleck Biochemicals) or NPS R-568 (Tocris) or equivalent amounts of DMSO (Sigma-Aldrich). Cell viability was evaluated after 72 hours by means of quantifying the percentage of viable cells by means of the Promega CellTiter 96(r) Aqueous One Solution Cell Proliferation Assay (MTS) system. It was thus observed that both drugs induced a decrease in cell viability in the 7 cell lines examined (FIG. 2), and that in 5 of said cell lines the $IC_{50}$ (drug concentration causing the death of 50% of the cells with respect to the control) of cinacalcet was less than that of NPS R-568 in a statistically significant manner (Table 1). In the case of SK-N-AS and LA1-55n cell lines, the difference in the effect promoted by both drugs was not statistically significant (Table 1).

TABLE 1

$IC_{50}$ values obtained after treating seven wild type neuroblastoma cell lines with cinacalcet or NPS R-568.

| Cell line | Cinacalcet | NPS R-568 | P value |
| --- | --- | --- | --- |
| LAN-1 | 17.19 | 24.81 | <0.0001 |
| SK-N-LP | 10.31 | 22.38 | <0.0001 |
| SK-N-JD | 10.92 | 25.82 | <0.0001 |
| SK-N-BE(2)C | 10.69 | 16.65 | <0.0001 |
| LA1-5s | 16.73 | 34.5 | <0.0001 |
| LA1-55n | 10.52 | 11.42 | Insignificant |
| SK-N-AS | 10.26 | 15.14 | Insignificant |

Example 3

Figure 3:
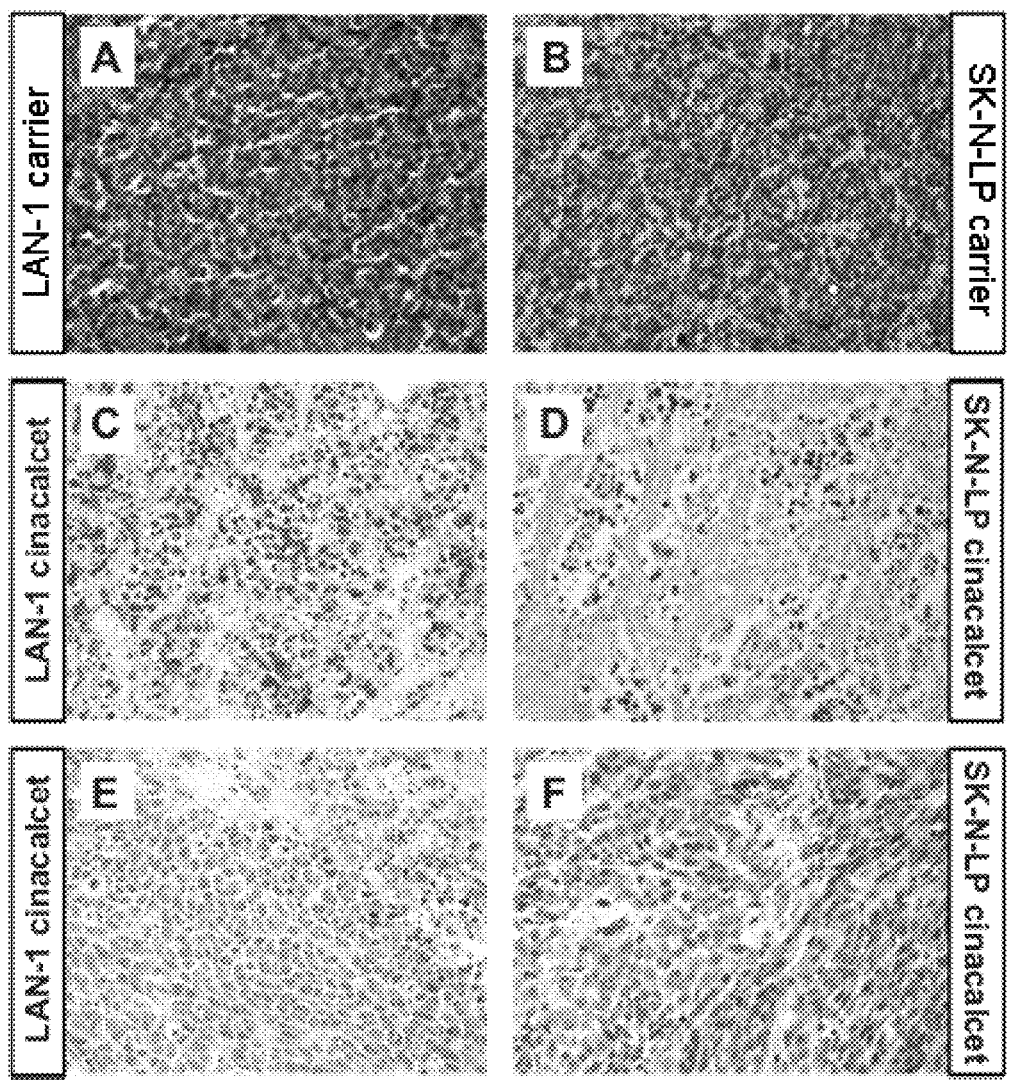
FIG. 3 shows the morphological examination of xenografts generated from the LAN-1 (FIGS. 3A, 3C, 3E) and SK-N-LP (FIGS. 3B, 3D, 3F) cell lines treated with cinacalcet (FIGS. 3C-3F) or not treated with cinacalcet (FIGS. 3A, 3B). Specimens in which cinacalcet caused mostly cell death (FIGS. 3C, 3D) or cytodifferentiation (FIGS. 3E, 3F) are shown.

Analysis of the Effects of Treatment with Cinacalcet in an In Vivo Model of Neuroblastoma Xenografts of LAN-1 and SK-N-LP cell lines were generated for which aliquots containing $10 \times 10^6$ cells from said cell lines were inoculated subcutaneously in 4-6 week old female athymic nu/nu mice (Charles Rivers). Starting from day 12, when the forming tumor could already be measured using Vernier calipers, oral treatment was started 6 days a week with cinacalcet 100 mg/kg (FIGS. 3C-3F) and with the carrier as a negative control (FIGS. 3A and 3B). The tumor volume was measured every 2-3 days. The mice were sacrificed after 40 days. Each tumor was weighed before being sectioned into two halves: one half was frozen in liquid nitrogen for expression analysis and the other half was fixed and embedded in paraffin for morphological examination and immunohistochemical analyses. In the morphological analysis of the xenografts of both cell lines treated with cinacalcet, specimens in which there were large areas with necrosis and/or apoptosis (FIGS. 3C and 3D) and/or morphological signs of differentiation in viable cells (FIGS. 3E and 3F) were observed.

The invention claimed is:

1. A method of treatment of a neuroblastic tumor in a human subject, the method comprising administering to the subject in need thereof a composition comprising a therapeutically effective amount of cinacalcet, wherein the active ingredient of the composition is cinacalcet alone.

2. The method according to claim 1, wherein the neuroblastic tumor is a neuroblastoma.

3. The method according to claim 1, wherein the neuroblastic tumor is a ganglioneuroblastoma.

4. The method according to claim 1, wherein the neuroblastic tumor is a ganglioneuroma.

* * * * *